United States Patent
Ducray et al.

(10) Patent No.: US 7,304,018 B2
(45) Date of Patent: Dec. 4, 2007

(54) AMIDOACETONITRILE COMPOUNDS AND THEIR USE AS PESTICIDES

(75) Inventors: Pierre Ducray, Village-Neuf (FR); Thomas Goebel, Lorrach (DE); Jacques Bouvier, Neuchatel (CH)

(73) Assignee: Novartis Animal Health US, Inc., Greensboro, NC (US)

( * ) Notice: Subject to any disclaimer, the term of this patent is extended or adjusted under 35 U.S.C. 154(b) by 550 days.

(21) Appl. No.: 10/514,300

(22) PCT Filed: Jun. 15, 2003

(86) PCT No.: PCT/EP03/05928

§ 371 (c)(1), (2), (4) Date: Nov. 12, 2004

(87) PCT Pub. No.: WO03/104187

PCT Pub. Date: Dec. 18, 2003

(65) Prior Publication Data

US 2005/0203178 A1    Sep. 15, 2005

(30) Foreign Application Priority Data

Jun. 6, 2002    (CH) .................................. 0965/02

(51) Int. Cl.
*A01N 37/34*    (2006.01)
*C07C 255/32*    (2006.01)

(52) U.S. Cl. ...................... 504/312; 558/303; 558/388; 558/390; 558/392; 504/309

(58) Field of Classification Search ................ 558/303, 558/388, 390, 392; 504/309, 312
See application file for complete search history.

(56) References Cited

U.S. PATENT DOCUMENTS 3,576,843 A * 4/1971 Model et al. ................ 560/138
6,239,077 B1 * 5/2001 Andoh et al. ................ 504/312

FOREIGN PATENT DOCUMENTS

EP    0 953 565    11/1999
FR    1 441 499    6/1966

* cited by examiner

*Primary Examiner*—Golam M. M. Shameem
(74) *Attorney, Agent, or Firm*—Kimberly H. Parker

(57) ABSTRACT

The invention relates to compounds of the general formula: (I) and optionally the enantiomers thereof. The active ingredients have advantages pesticidal properties. They are especially suitable for controlling parasites on warm-blooded animals.

25 Claims, No Drawings

AMIDOACETONITRILE COMPOUNDS AND THEIR USE AS PESTICIDES

This application is a National Phase Application under § 371 of International Application Number PCT/EP03/05928 filed on Jun. 5, 2003.

The present invention relates to new amidoaceniltrile of formula

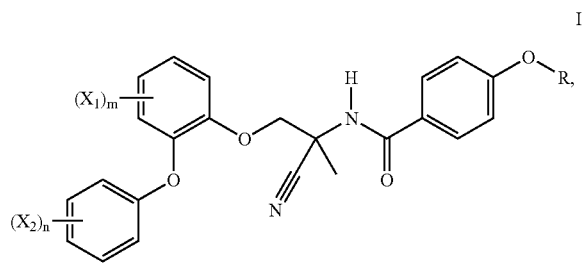

wherein
R signifies $C_1$-$C_6$-alkyl, halo-$C_1$-$C_6$-alkyl, $C_1$-$C_6$-alkoxy-$C_2$-$C_6$-alkyl or halo-$C_1$-$C_6$-alkoxy-halo-$C_2$-$C_6$-alkyl;
$X_1$ signifies halogen, whereby if m is greater than 1, $X_1$ may be variable halogen;
$X_2$ signifies halogen, whereby if n is greater than 1, $X_2$ may be variable halogen;
m signifies 1, 2, 3 or 4; and
n is 1, 2, 3, 4 or 5;

optionally diastereoisomers, E/Z-isomers, E/Z-isomer mixtures and/or tautomers, each respectively in free form or in salt form, their preparation and usage in the control of endo- and ectoparasites, especially helminths, in and on warm-blooded animals, especially productive livestock and domestic animals, as well as on plants, furthermore pesticides which contain at least one of these compounds.

Substituted amidoacetonitrile compounds having pesticidal activity are described for example in EP-0.953.565 A2. However, the active ingredients specifically disclosed therein cannot always fulfill the requirements regarding potency and activity spectrum. There is therefore a need for active ingredients with improved pesticidal properties. It has now been found that the amidoacetonitrile compounds of formula I have excellent pesticidal properties, especially against endo- and ecto-parasites in and on warm-blooded animals and plants.

Alkyl—as a group per se and as structural element of other groups and compounds, for example haloalkyl and alkoxy,—is, in each case with due consideration of the specific number of carbon atoms in the group or compound in question, either straight-chained, i.e. methyl, ethyl, propyl, butyl, pentyl or hexyl, or branched, e.g. isopropyl, isobutyl, sec.-butyl, tert.-butyl, isopentyl, neopentyl or isohexyl.

Halogen—as a group per se and as structural element of other groups and compounds such as haloalkyl, or haloalkoxy,—is fluorine, chlorine, bromine or iodine, especially fluorine, chlorine or bromine, in particular fluorine or chlorine.

Halogen-substituted carbon-containing groups and compounds, such as haloalkyl or halo-alkoxy, may be partially halogenated or perhalogenated, whereby in the case of multiple halogenation, the halogen substituents may be identical or different. Examples of halogen-alkyl—as a group per se and as structural element of other groups and compounds such as haloalkoxy or haloalkylthio,—are methyl which is mono- to trisubstituted by fluorine, chlorine and/or bromine, such as $CHF_2$ or $CF_3$; ethyl which is mono—to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CF_2CHBr_2$, $CF_2CHClF$, $CF_2CHBrF$ or $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$ or $CH(CF_3)_2$; butyl or one of its isomers, mono- to nonasubstituted by fluorine, chlorine and/or bromine, such as $CF(CF_3)CHFCF_3$ or $CH_2(CF_2)_2CF_3$; pentyl or one of its isomers substituted once to eleven times by fluorine, chlorine and/or bromine, such as $CF(CF_3)(CHF)_2CF_3$ or $CH_2(CF_2)_3CF_3$; and hexyl or one of its isomers substituted once to thirteen times by fluorine, chlorine and/or bromine, such as $(CH_2)_4CHBrCH_2Br$, $CF_2(CHF)_4CF_3$, $CH_2(CF_2)_4CF_3$ or $C(CF_3)_2(CHF)_2CF_3$.

Alkoxy groups preferably have a chain length of 1 to 6 carbon atoms. Alkoxy is for example methoxy, ethoxy, propoxy, isopropoxy, n-butoxy, isobutoxy, sec.-butoxy and tert.-butoxy, as well as the isomers pentyloxy and hexyloxy; preferably methoxy and ethoxy. Haloalkoxy groups preferably have a chain length of 1 to 6 carbon atoms. Haloalkoxy is e.g. fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy.

Preferred embodiments within the scope of the invention are:
(1) A compound of formula I, wherein R is $C_1$-$C_6$-alkyl or halo-$C_1$-$C_6$-alkyl;
especially halo-$C_1$-$C_4$-alkyl;
most particularly halo-$C_1$-$C_2$-alkyl;
(2) A compound of formula 1, wherein $X_1$ is chlorine or fluorine;
especially chlorine;
(3) A compound of formula 1, wherein $X_2$ is chlorine or fluorine;
especially chlorine;
(4) A compound of formula 1, wherein m is 1, 2 or 3;
especially 1 or 2;
particularly 1;
(5) A compound of formula I, wherein n is 1, 2 or 3;
especially 1 or 2;
particularly 2;
(6) A compound of formula I, wherein
R signifies $C_1$-$C_6$-alkyl or halo-$C_1$-$C_6$-alkyl;
$X_1$ signifies chlorine or fluorine;
$X_2$ signifies chlorine or fluorine;
m is 1, 2 or 3 and
n is 1, 2 or 3;
(7) A compound of formula I, wherein
R is halo-$C_1$-$C_4$-alkyl;
$X_1$ and $X_2$ are chlorine;
m is 1 or 2, and
n is 1 or 2;
(8) A compound of formula I, wherein
R is halo-$C_1$-$C_2$-alkyl;
$X_1$ and $X_2$ are chlorine;
m is 1, and
n is 2.

Within the context of the invention, particular preference is given to the compounds of formula I listed in Table 1, and most particularly those named in the synthesis examples.

A further object of the invention is the process for the preparation of the compounds of formula I, respectively In free form or in salt form, for example characterized In that a compound of formula

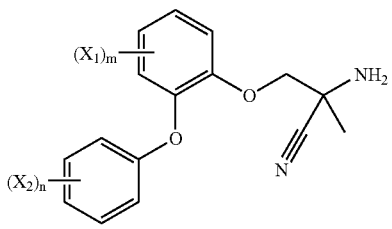

which is known or may be produced analogously to corresponding known compounds, and wherein $X_1$, $X_2$, m and n are defined as given for formula I, is reacted with a compound of formula

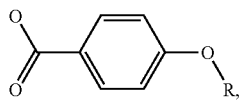

which is known or may be prepared analogously to corresponding known compounds, and wherein R is defined as given for formula I and Q is a leaving group, optionally in the presence of a basic catalyst, and if desired, a compound of formula I obtainable according to the method or in another way, respectively in free form or in salt form, is converted into another compound of formula I, a mixture of isomers obtainable according to the method is separated and the desired isomer isolated and/or a free compound of formula I obtainable according to the method is converted into a salt or a salt of a compound of formula I obtainable according to the method is converted into the free compound of formula I or into another salt.

What has been stated above for salts of compounds I also applies analogously to salts of the starting materials listed hereinabove and hereinbelow.

The reaction partners can be reacted with one another as they are, i.e. without the addition of a solvent or diluent, e.g. in the melt. In most cases, however, the addition of an inert solvent or diluent, or a mixture thereof, is of advantage. Examples of such solvents or diluents are: aromatic, aliphatic and alicyclic hydrocarbons and halogenated hydrocarbons, such as benzene, toluene, xylene, mesitylene, tetraline, chlorobenzene, dichlorobenzene, bromobenzene, petroleum ether, hexane, cyclohexane, dichloromethane, trichloromethane, tetrachloromethane, dichloroethane, trichloroethene or tetrachloroethene; ethers, such as diethyl ether, dipropyl ether, diisopropyl ether, dibutyl ether, tert-butyl methyl ether, ethylene glycol monomethyl ether, ethylene glycol monoethyl ether, ethylene glycol dimethylether, dimethoxydiethylether, tetrahydrofuran or dioxane; ketones such as acetone, methyl ethyl ketone or methyl isobutyl ketone; amides such as N,N-dimethylformamide, N,N-diethyl-formamide, N,N-dimethylacetamide, N-methylpyrrolidone or hexamethylphosphoric acid triamide; nitriles such as acetonitrile or propionitrile; and sulfoxides, such as dimethy sulfoxide.

Preferred leaving groups Q are halogens, tosylates, mesylates and triflates, most preferably halogens, especially chlorine.

Suitable bases for facilitating the reaction are e.g. alkali metal or alkaline earth metal hydroxides, hydrides, amides, alkanolates, acetates, carbonates, diakylamides or alkylsilylamides; alkylamines, alkylenediamines, optionally N-alkylated, optionally unsaturated, cyclo-alkylamines, basic heterocycles, ammonium hydroxides, as well as carbocyclic amines. Those which may be mentioned by way of example are sodium hydroxide, hydride, amide, methanolate, acetate, carbonate, potassium tert.-butanolate, hydroxide, carbonate, hydride, lithium diisopropylamide, potassium bis(trimethylsilyl)-amide, calcium hydride, triethylamine, diisopropylethylamine, triethylenediamine, cyclohexylamine, N-cyclohexyl-N,N-dimethyl-amine, N,N-diethylaniline, pyridine, 4-(N,N-dimethylamino)pyridine, quinuclidine, N-methylmorpholine, benzyltrimethylammonium hydroxide, as well as 1,5-diazabicyclo[5.4.0]undec-5-ene (DBU). Preference is given to diisopropylethylamine and 4-(N,N-dimethylamino) pyridine.

The reaction advantageously takes place in a temperature range of ca. 0° C. to ca. 100° C., preferably from ca. 10° C. to ca. 40° C.

A further object of the invention is the process for the preparation of the compounds of formula II, respectively in free form or in salt form, for example characterized in that a compound of formula

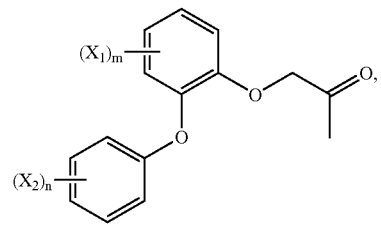

which is known or may be prepared analogously to corresponding known compounds, and wherein $X_1$, $X_2$, m and n are defined as given for formula I, is reacted with an inorganic or organic cyanide and $NH_3$, and if desired, a compound of formula II obtainable according to the method or in another way, respectively in free form or in salt form, is converted into another compound of formula II, a mixture of isomers obtainable according to the method is separated and the desired isomer isolated and/or a free compound of formula II obtainable according to the method is converted into a salt or a salt of a compound of formula II obtainable according to the method is converted into the free compound of formula II or into another salt.

Suitable cyanides are sodium cyanide, potassium cyanide, trimethylsilyl cyanide and acetone cyanohydrin.

The general method for reacting carbonyl compounds, e.g. of formula IV, with cyanides and amines, e.g. of formula $R_6$—$NH_2$, is a Strecker reaction, for example as in Organic Synthesis Coll. Vol. 3, 88 (1973).

Salts of compounds I may be produced in known manner. Acid addition salts of compounds I, for example, are obtainable by treatment with a suitable acid or a suitable ion exchange reagent, and salts with bases are obtainable by treatment with a suitable base or a suitable ion exchange reagent.

Salts of compounds I can be converted into the free compounds I by the usual means, acid addition salts e.g. by treating with a suitable basic composition or with a suitable ion exchange reagent, and salts with bases e.g. by treating with a suitable acid or a suitable ion exchange reagent.

Salts of compounds I can be converted into other salts of compounds I in a known manner; acid addition salts can be converted for example into other acid addition salts, e.g. by treating a salt of an inorganic acid, such as a hydrochloride, with a suitable metal salt, such as a sodium, barium, or silver salt, of an acid, e.g. with silver acetate, in a suitable solvent, in which a resulting inorganic salt, e.g. silver chloride, is insoluble and thus precipitates out from the reaction mixture.

Depending on the method and/or reaction conditions, compounds I with salt-forming characteristics can be obtained in free form or in the form of salts.

Compounds I can also be obtained in the form of their hydrates and/or also can include other solvents, used for example where necessary for the crystallisation of compounds present in solid form.

The compounds I may be optionally present as optical and/or geometric isomers or as a mixture thereof. The invention relates both to the pure isomers and to all possible isomeric mixtures, and is hereinbefore and hereinafter understood as doing so, even if stereochemical details are not specifically mentioned in every case.

Diastereoisomeric mixtures of compounds I, which are obtainable by the process or in another way, may be separated in known manner, on the basis of the physical-chemical differences in their components, into the pure diastereoisomers, for example by fractional crystallisation, distillation and/or chromatography.

Splitting of mixtures of enantiomers, that are obtainable accordingly, into the pure isomers, may be achieved by known methods, for example by recrystallisation from an optically active solvent, by chromatography on chiral adsorbents, e.g. high-pressure liquid chromatography (HPLC) on acetyl cellulose, with the assistance of appropriate microorganisms, by cleavage with specific immobilized enzymes, through the formation of inclusion compounds, e.g. using chiral crown ethers, whereby only one enantiomer is complexed.

According to the invention, apart from separation of corresponding isomer mixtures, generally known methods of diastereoselective or enantioselective synthesis can also be applied to obtain pure diastereoisomers or enantiomers, e.g. by carrying out the method of the invention using educts with correspondingly suitable stereochemistry.

It is advantageous to isolate or synthesise the biologically more active isomer, e.g. enantiomer, provided that the individual components have differing biological efficacy.

In the method of the present invention, the starting materials and intermediates used are preferably those that lead to the compounds I described at the beginning as being especially useful.

The invention relates in particular to the preparation method described in the examples.

Starting materials and intermediates, which are new and are used according to the invention for the preparation of compounds I, as well as their usage and process for the preparation thereof, similarly form an object of the invention.

The compounds I according to the invention are notable for their broad activity spectrum and are valuable active ingredients for use in pest control, including in particular the control of endo- and ecto-parasites, especially helminths, in and on warm-blooded animals, especially livestock and domestic animals, and also on plants, whilst being well-tolerated by warm-blooded animals, fish and plants.

In the context of the present invention, ectoparasites are understood to be in particular insects, mites and ticks. These include insects of the order: *Lepidoptera, Coleoptera, Homoptera, Heteroptera, Diptera, Thysanoptera, Orthoptera, Anoplura, Siphonaptera, Mallophaga, Thysanura, Isoptera, Psocoptera* and *Hymenoptera*. However, the ectoparasites which may be mentioned in particular are those which trouble humans or animals and carry pathogens, for example flies such as *Musca domestica, Musca vetustissima, Musca autumnalis, Fannia canicularis, Sarcophaga camaria, Lucilia cuprina, Hypoderma bovis, Hypoderma lineatum, Chrysomyia chloropyga, Dermatobia hominis, Cochliomyia hominivorax, Gasterophilus intestinalis, Oestrus ovis, Stomoxys calcitrans, Haematobla irritans* and midges (*Nematocera*), such as *Culicidae, Simulildae, Psychodidae*, but also blood-sucking parasites, for example fleas, such as *Ctenocephalides* fells and *Ctenocephalides canis* (cat and dog fleas), *Xenopsylla cheopis, Pulex irritans, Dermatophilus penetrans*, lice, such as *Damalina ovis, Pediculus humanis*, biting flies and horse-flies (*Tabanidae*), *Haematopota* spp. such as *Haematopota pluvialis, Tabanidea* spp. such as *Tabanus nigrovittatus, Chrysopsinae* spp. such as *Chrysops caecutiens*, tsetse flies, such as species of *Glossinia*, biting insects, particularly cockroaches, such as *Blatella germanaca, Blatta orientalis, Periplaneta americana*, mites, such as *Dermanyssus gallinae, Sarcoptes scabiei, Psoroptes ovis* and *Psorergates* spp. and last but not least ticks. The latter belong to the order *Acarina*. Known representatives of ticks are, for example, *Boophilus, Amblyomma, Anocentor, Dermacentor, Haemaphysalis, Hyalomma, Ixodes, Rhipicentor, Margaropus, Rhipicephalus, Argas, Otobius* and *Ornithodoros* and the like, which preferably infest warm-blooded animals including farm animals, such as cattle, pigs, sheep and goats, poultry such as chickens, turkeys and geese, fur-bearing animals such as mink, foxes, chinchillas, rabbits and the like, as well as domestic animals such as cats and dogs, but also humans.

The compounds I according to the invention are also active against all or individual development stages of animal pests showing normal sensitivity, as well as those showing resistance, such as insects and members of the order *Acarina*. The insecticidal, ovicidal and/or acaricidal effect of the active substances of the invention can manifest itself directly, i.e. killing the pests either immediately or after some time has elapsed, for example when moulting occurs, or by destroying their eggs, or indirectly, e.g. reducing the number of eggs laid and/or the hatching rate, good efficacy corresponding to a pesticidal rate (mortality) of at least 50 to 60%.

Compounds I can also be used against hygiene pests, especially of the order Diptera of the families Sarcophagidae, Anophilldae and Culicidae; the orders Orthoptera, Dictyoptera (e.g. the family Biattidae) and Hymenoptera (e.g. the family Formicidae).

Compounds I also have sustainable efficacy on parasitic mites and insects of plants. In the case of spider mites of the order Acarina, they are effective against eggs, nymphs and adults of Tetranychidae (*Tetranychus*spp. and *Panonychus*-spp.).

They have high activity against sucking insects of the order Homoptera, especially against pests of the families Aphididae, Delphacidae, Cicadellidae, Psyllidae, Loccidae, Diaspididae and Erlophydidae (e.g. rust mite on citrus fruits); the orders Hemiptera, Heteroptera and Thysanoptera, and on the plant-eating insects of the orders Lepidoptera, Coleoptera, Diptera and Orthoptera They are similarly suitable as a soil insecticide against pests in the soil.

The compounds of formula I are therefore effective against all stages of development of sucking insects and eating insects on crops such as cereals, cotton, rice, maize, soya, potatoes, vegetables, fruit, tobacco, hops, citrus, avocados and other crops.

The compounds of formula I are also effective against plant nematodes of the species *Meloidogyne, Heterodera, Pratylenchus, Ditylenchus, Radopholus, Rizoglyphus* etc.

In particular, the compounds are effective against helminths, in which the endoparasitic nematodes and trematodes may be the cause of serious diseases of mammals and poultry, e.g. sheep, pigs, goats, cattle, horses, donkeys, dogs, cats, guinea-pigs and exotic birds. Typical nematodes of this indication are: *Haemonchus, Trichostrongylus, Ostertagia, Nematodirus, Cooperia, Ascaris, Bunostonum, Oesophagostonum, Charbertia, Trichuris, Strongylus, Trichonema, Dictyocaulus, Capillaria, Heterakis, Toxocara, Ascaridia, Oxyuris, Ancylostoma, Uncinaria, Toxascaris* and *Parascaris*. The trematodes include, in particular, the family of Fasciolideae, especially *Fasciola hepatica*.

It could also be shown surprisingly and unexpectedly that the compounds of formula I have exceptionally high efficacy against nematodes that are resistant to many active substances. This can be demonstrated in vitro by the LDA test and in vivo for example in Mongolian gerbils and sheep. It was shown that amounts of active substance which kill sensitive strains of *Haemonchus contortus* or *Trichostrongylus colubriformis*, are also sufficiently effective at controlling corresponding strains that are resistant to benzimidazoles, levamisol and macrocyclic lactones (for example ivermectin).

Certain pests of the species *Nematodirus, Cooperia* and *Oesophagostonum* infest the intestinal tract of the host animal, while others of the species *Haemonchus* and *Ostertagia* are parasitic in the stomach and those of the species *Dictyocaulus* are parasitic in the lung tissue. Parasites of the families Filardidae and Setariidae may be found in the internal cell tissue and in the organs, e.g. the heart, the blood vessels, the lymph vessels and the subcutaneous tissue. A particularly notable parasite is the heartworm of the dog, *Dirofilaria immitis*. The compounds of formula I are highly effective against these parasites.

The pests which may be controlled by the compounds of formula I also include those from the class of Cestoda (tapeworms), e.g. the families Mesocestoidae, especially of the genus *Mesocestoides*, in particular *M. lineatus; Dilepidide*, especially *Dipylidium caninum, Joyeuxiella* spp., in particular *Joyeuxiella pasquali*, and *Diplopylidium* spp., and *Taenlidae*, especially *Taenia pisiformis, Taehia cervi, Taenia ovis, Tanela hydatigena, Taenia multiceps, Taenia taeniaeformis, Taenia serialis*, and *Echinocuccus* spp., most preferably *Taneia hydatigena, Taenia ovis, Taenia multiceps, Taenia serialis; Echinocuccus granulosus* and *Echinococcus granulosus* and *Echinococcus multilocularis*, as well as *Multiceps multiceps*.

The compounds of formula I are also suitable for the control of *Coccidiose*, which can appear especially on piglets and chickens. Apart from *Coli* bacteria and *Clostridiae, Coccidiae* are one of the most important causes of diarrhoea of unweaned piglets. The most important type in the case of piglets is *Isospora suls*. The piglets become infected with the oocysts (spores) of *Isospora suis* through the mouth. The oocysts migrate into the small intestine, where they penetrate into the small intestinal mucosa. There, they pass through various stages of development. Between the fifth and ninth and the 11th to 14th day after infection, the *Coccidiae* emerge from the intestinal mucosa and are then detectable again in the faeces. This outbreak causes great damage to the intestinal mucosa. The piglets react by exhibiting partly yellowish—pasty to watery diarrhoea. It has a rancid small. Occasionally, individual piglets vomit. It is customary for the diarrhoea to occur between the eighth and fifteenth day of age.

Most particularly, *Taenia hydatigena, T. pisiformis, T. ovis, T. taeniaeformis, Multiceps multiceps, Joyeuxiella pasquali, Dipylidium caninum, Mesocestoides* spp., *Echinococcus granulosus* and *E. multilocularis* are controlled on or in dogs and cats simultaneously with *Dirofilaria immitis, Ancylostoma* ssp., *Toxocara* ssp. and/or *Trichuris vulpis*. Equally preferred, *Ctenocephalides felis* and/or *C. canis* are simultaneously controlled with the above-mentioned nematodes and cestodes.

Furthermore, the compounds of formula I are suitable for the control of human pathogenic parasites. Of these, typical representatives that appear in the digestive tract are those of the species *Ancylostoma, Necator, Ascadis, Strongyloides, Trichinella, Capillaria, Trichuis* and *Enterobius*. The compounds of the present Invention are also effective against parasites of the species *Wuchereria, Brugia, Onchocerca* and *Loa* from the family of Filardidae, which appear in the blood, in the tissue and in various organs, and also against *Dracunculus* and parasites of the species *Strongyloides* and *Trichinella*, which infect the gastrointestinal tract in particular.

In addition, the compounds of formula I are also effective against harmful and pathogenic fungi on plants, as well as on humans and animals.

The good pesticidal activity of the compounds of formula I according to the invention corresponds to a mortality rate of at least 50-60% of the pests mentioned. In particular, the compounds of formula I are notable for the exceptionally long duration of efficacy.

The compounds of formula I are preferably employed in unmodified form or preferably together with the adjuvants conventionally used in the art of formulation and may therefore be processed in a known manner to give, for example, emulsifiable concentrates, directly dilutable solutions, dilute emulsions, soluble powders, granules or microencapsulations in polymeric substances. As with the compositions, the methods of application are selected in accordance with the intended objectives and the prevailing circumstances.

The formulation, i.e. the agents, preparations or compositions containing the active ingredient of formula I, or combinations of these active ingredients with other active ingredients, and optionally a solid or liquid adjuvant, are produced in a manner known per se, for example by intimately mixing and/or grinding the active ingredients with spreading compositions, for example with solvents, solid carriers, and optionally surface-active compounds (surfactants).

The solvents in question may be: alcohols, such as ethanol, propanol or butanol, and glycols and their ethers and esters, such as propylene glycol, dipropylene glycol ether, ethylene glycol, ethylene glycol monomethyl or -ethyl ether, ketones, such as cyclohexanone, isophorone or diacetanol alcohol, strong polar solvents, such as N-methyl-2-pyrrolidone, dimethyl sulfoxide or dimethylformamide, or water, vegetable oils, such as rape, castor, coconut, or soybean oil, and also, if appropriate, silicone oils.

Preferred application forms for usage on warm-blooded animals in the control of helminths include solutions, emulsions, suspensions (drenches), food additives, powders, tablets including effervescent tablets, boli, capsules, microcapsules and pour-on formulations, whereby the physiological compatibility of the formulation excipients must be taken into consideration.

The binders for tablets and boli may be chemically modified polymeric natural substances that are soluble in water or in alcohol, such as starch, cellulose or protein derivatives (e.g. methyl cellulose, carboxymethyl cellulose, ethylhydroxyethyl cellulose, proteins such as zein, gelatin and the like), as well as synthetic polymers, such as polyvinyl alcohol, polyvinyl pyrrolidone etc. The tablets also contain fillers (e.g. starch, microcrystalline cellulose, sugar, lactose etc.), glidants and disintegrants.

If the anthelminthics are present in the form of feed concentrates, then the carriers used are e.g. performance feeds, feed grain or protein concentrates. Such feed concentrates or compositions may contain, apart from the active ingredients, also additives, vitamins, antibiotics, chemotherapeutics or other pesticides, primarily bacteriostats, fungistats, coccidiostats, or even hormone preparations, substances having anabolic action or substances which promote growth, which affect the quality of meat of animals for slaughter or which are beneficial to the organism in another way. If the compositions or the active ingredients of formula I contained therein are added directly to feed or to the drinking troughs, then the formulated feed or drink contains the active ingredients preferably in a concentration of ca. 0.0005 to 0.02% by weight (5-200 ppm).

The compounds of formula I according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents. If the range of activity is to be extended to endoparasites, e.g. wormers, the compounds of formula I are suitably combined with substances having endoparasitic properties. Of course, they can also be used in combination with antibacterial compositions. Since the compounds of formula I are adulticides, i.e. since they are effective in particular against the adult stages of the target parasites, the addition of pesticides which instead attack the juvenile stages of the parasites may be very advantageous. In this way, the greatest part of those parasites that produce great economic damage will be covered. Moreover, this action will contribute substantially to avoiding the formation of resistance. Many combinations may also lead to synergistic effects, i.e. the total amount of active ingredient can be reduced, which is desirable from an ecological point of view. Preferred groups of combination partners and especially preferred combination partners are named in the following, whereby combinations may contain one or more of these partners in addition to a compound of formula I.

Suitable partners in the mixture may be biocides, e.g. the insecticides and acaricides with a varying mechanism of activity, which are named in the following and have been known to the person skilled in the art for a long time, e.g. chitin synthesis inhibitors, growth regulators; active ingredients which act as juvenile hormones; active ingredients which act as adulticides; broad-band insecticides, broad-band acaricides and nematicides; and also the well known anthelminthics and insect- and/or acarid-deterring substances, said repellents or detachers.

Non-limitative examples of suitable insecticides and acaricides are:

1. Abamectin
2. AC 303 630
3. Acephat
4. Acrinathrin
5. Alanycarb
6. Aldicarb
7. α-Cypermethrin
8. Alphamethrin
9. Amitraz
10. Avermectin $B_1$
11. AZ 60541
12. Azinphos A
13. Azinphos M
14. Azocyclotin
15. *Bacillus subtil.* toxin
16. Bendiocarb
17. Benfuracarb
18. Bensultap
19. β-Cyfluthrin
20. Bifenthrin
21. BPMC
22. Brofenprox
23. Bromophos A
24. Bufencarb
25. Buprofezin
26. Butocarboxim
27. Butylpyridaben
28. Cadusafos
29. Carbaryl
30. Carbofuran
31. Carbophenothion
32. Cartap
33. Cloethocarb
34. Chlorethoxyfos
35. Chlorfenapyr
36. Chlorfluazuron
37. Chlormephos
38. Chlorpyrifos
39. Cis-Resmethrin
40. Clocythrin
41. Clofentezin
42. Cyanophos
43. Cycloprothrin
44. Cyfluthrin
45. Cyhexatin
46. D 2341
47. Deltamethrin
48. Demeton M
49. Demeton S
50. Demeton-S-methyl
51. Dichlofenthion
52. Dicliphos
53. Diethion
54. Diflubenzuron
55. Dimethoat
56. Dimethylvinphos
57. Dioxathion
58. DPX-MP062
59. Edifenphos
60. Emamectin
61. Endosulfan
62. Esfenvalerat
63. Ethiofencarb
64. Ethion
65. Ethofenprox
66. Ethoprophos
67. Etrimfos
68. Fenamiphos
69. Fenazaquin
70. Fenbutatinoxid
71. Fenitrothion
72. Fenobucarb
73. Fenothiocarb
74. Fenoxycarb
75. Fenpropathrin
76. Fenpyrad -continued 77. Fenpyroximate
78. Fenthion
79. Fenvalerate
80. Fipronil
81. Fluazinam
82. Fluazuron
83. Flucycloxuron
84. Flucythrinat
85. Flufenoxuron
86. Flufenprox
87. Fonofos
88. Formothion
89. Fosthiazat
90. Fubfenprox
91. HCH
92. Heptenophos
93. Hexaflumuron
94. Hexythiazox
95. Hydroprene
96. Imidacloprid
97. insect-active fungi
98. insect-active nematodes
99. insect-active viruses
100. Iprobenfos
101. Isofenphos
102. Isoprocarb
103. Isoxathion
104. Ivermectin
105. λ-Cyhalothrin
106. Lufenuron
107. Malathion
108. Mecarbam
109. Mesulfenfos
110. Metaldehyd
111. Methamidophos
112. Methiocarb
113. Methomyl
114. Methoprene
115. Metolcarb
116. Mevinphos
117. Milbemectin
118. Moxidectin
119. Naled
120. NC 184
121. NI-25, Acetamiprid
122. Nitenpyram
123. Omethoat
124. Oxamyl
125. Oxydemeton M
126. Oxydeprofos
127. Parathion
128. Parathion-methyl
129. Permethrin
130. Phenthoat
131. Phorat
132. Phosalone
133. Phosmet
134. Phoxim
135. Pirimicarb
136. Pirimiphos A
137. Pirimiphos M
138. Promecarb
139. Propaphos
140. Propoxur
141. Prothiofos
142. Prothoat
143. Pyrachlofos
144. Pyradaphenthion
145. Pyresmethrin
146. Pyrethrum
147. Pyridaben
148. Pyrimidifen
149. Pyriproxyfen
150. RH 5992
151. RH-2485
152. Salithion
153. Sebufos -continued 154. Silafluofen
155. Spinosad
156. Sulfotep
157. Sulprofos
158. Tebufenozide
159. Tebufenpyrad
160. Tebupirimfos
161. Teflubenzuron
162. Tefluthrin
163. Temephos
164. Terbam
165. Terbufos
166. Tetrachlorvinphos
167. Thiafenox
168. Thiodicarb
169. Thiofanox
170. Thionazin
171. Thuringiensin
172. Tralomethrin
173. Triarathene
174. Triazamate
175. Triazophos
176. Triazuron
177. Trichlorfon
178. Triflumuron
179. Trimethacarb
180. Vamidothion
181. XMC (3,5,-Xylyl-methylcarbamat)
182. Xylylcarb
183. YI 5301/5302
184. ζ-Cypermethrin
185. Zetamethrin Non-limitative examples of suitable anthelminthics are named in the following, a few representatives have insecticidal and acaricidal activity in addition to the anthelminthic activity, and are partly already in the above list.

(A1) Praziguantel=2-cyclohexylcarbonyl-4-oxo-1,2,3,6,7,11b-hexahydro-4H-pyrazino[2,1-α]isoquinoline (A2) Closantel=3,5-dilodo-N-[5-chloro-2-methyl-4-(a-cyano-4-chlorobenzyl)phenyl]-salicylamide (A3) Triclabendazole=5-chloro-6-(2,3-dichlorophenoxy)-2-methylthio-1H-benzimidazole (A4) Levamisol=L-(−)-2,3,5,6-tetrahydro-6-phenylimidazo[2,1b]thiazole (A5) Mebendazole=(5-benzoyl-1H-benzimidazol-2-yl)carbaminic acid methylester (A6) Omphalotin=a macrocyclic fermentation product of the fungus *Omphalotus olearius* described in WO 97/20857

(A7) Abamectin=avermectin B1

(A8) Ivermectin=22,23-dihydroavermectin B1

(A9) Moxidectin=5-O-demethyl-28-deoxy-25-(1,3-dimethyl-1-butenyl)-6,28-epoxy-23-(methoxyimino)-milbemycin B (A10) Doramectin=25-cyclohexyl-5-O-demethyl-25-de(1-methylpropyl)-avermectin A1a (A11) Milbemectin=mixture of milbemycin A3 and milbemycin A4

(A12) Milbemycinoxim=5-oxime of milbemectin

Non-limitative examples of suitable repellents and detachers are:

(R1) DEET (N,N-diethyl-m-toluamide)

(R2) KBR 3023 N-butyl-2-oxycarbonyl-(2-hydroxy)-piperidine (R3) Cymiazole=N,-2,3-dihydro-3-methyl-1,3-thiazol-2-ylidene-2,4-xylidene The said partners in the mixture are best known to specialists in this field. Most are described in various editions of the Pesticide Manual, The British Crop Protection Council, London, and others In the various editions of The Merck Index, Merck & Co., Inc., Rahway, N.J., USA or in patent literature. Therefore, the following listing is restricted to a few places where they may be found by way of example.

(I) 2-Methyl-2-(methylthio)propionaldehyde-O-methylcarbamoyloxime (Aldicarb), from The Pesticide Manual, 11th Ed. (1997), The British Crop Protection Council, London, page 26;

(II) S-(3,4-dihydro-4-oxobenzo[d]-[1,2,3]-triazin-3-ylmethyl)O,O-dimethyl-phosphoro-dithioate (Azinphos-methyl), from The Pesticide Manual, 11th Ed. (1997), The British Crop Protection Council, London, page 67;

(III) Ethyl-N-[2,3-dihydro-2,2-dimethylbenzofuran-7-yloxycarbonyl-(methyl)aminothio]-N-isopropyl-β-alaninate (Benfuracarb), from The Pesticide Manual, 11th Ed. (1997), The British Crop Protection Council, London, page 96;

(IV) 2-Methylbiphenyl-3-ylmethyl-(Z)-(1RS)-cis-3-(2-chloro-3,3,3-trifluoroprop-1-enyl)-2,2-dimethylcyclopropanecarboxylate (Bifenthrin) The Pesticide Manual, 11th Ed. (1997), The British Crop Protection Council, London, page 118;

(V) 2-tert-butylimino-3-isopropyl-5-phenyl-1,3,5-thiadiazian-4-one (Buprofezin), from The Pesticide Manual, 11th Ed. (1997), The British Crop Protection Council, London, page 157;

(VI) 2,3-Dihydro-2,2-dimethylbenzofuran-7-yl-methylcarbamate (Carbofuran), from The Pesticide Manual, 11th Ed. (1997), The British Crop Protection Council, London, page 186;

(VII) 2,3-Dihydro-2,2-dimethylbenzofuran-7-yl-(dibutylaminothio)methylcarbamate (Carbosulfan), from The Pesticide Manual, 11th Ed. (1997), The British Crop Protection Council, London, page 188;

(VIII) S,S-(2-dimethylaminotrimethylene)-bis(thiocarbamate) (Cartap), from The Pesticide Manual, 11th Ed. (1997), The British Crop Protection Council, London, page 193;

(IX) 1-[3,5-Dichloro-4-(3-chloro-5-trifluoromethyl-2-pyridyloxy)phenyl]-3-(2,6-difluoro-benzoyl)-urea (Chlorfluazuron), from The Pesticide Manual, 11th Ed. (1997), The British Crop Protection Council, London, page 213;

(X) O,O-diethyl-O-3,5,6-trichloro-2-pyridyl-phosphorothioate (Chlorpyrifos), from The Pesticide Manual, 11th Ed. (1997), The British Crop Protection Council, London, page 235;

(XI) (RS)-α-cyano-4-fluoro-3-phenoxybenzyl-(1RS,3RS; 1RS,3RS)-3-(2,2-dichlorovinyl)-2,2-di-methylcyclopropanenecarboxylate (Cyfluthrin), from The Pesticide Manual, 11th Ed. (1997), The British Crop Protection Council, London, page 293;

(XII) Mixture of (S)-α-cyano-3-phenoxybenzyl-(Z)-(1R, 3R)-3-(2-chloro-3,3,3-trifluoro-propenyl)-2,2-dimethyl-cyclopropanecarboxy;ate and (R)-α-cyano-3-phenoxy-benzyl-(Z)-(1R,3)-3-(2-chloro-3,3,3-trifluoropropenyl)-2,2-dimethylcyclopropanecarboxylate (Lambda-Cyhalothrin), from The Pesticide Manual, 11th Ed. (1997), The British Crop Protection Council, London, page 300;

(XIII) Racemate consisting of (S)-α-cyano-3-phenoxybenzyl-(Z)-(1R,3R)-3-(2,2-dichlorovinyl)-2,2-dimethylcycopropanecarboxylate and (R)-α-cyano-3-phenoxybenzyl-(1S,3S)-3-(2,2-dichlorovinyl)-2,2-dimethylcyclopropanecarboxylate(Alpha-cypermethrin), from The Pesticide Manual, 11th Ed. (1997), The British Crop Protection Manual, Londo page 308;

(XIV) a mixture of the stereoisomers of (S)-α-cyano-3-phenoxybenzyl (1RS,3RS,-1 RS,3RS)-3-(2,2from The Pesticide Manual, 11th Ed. (1997), The British Crop Protection Council, London, page 314;

(XV) (S)-α-cyano-3-phenoxybenzyl-(1R,3R)-3-(2,2-dibromovinyl)-2,2-dimethylcyclopropane-carboxylate (Deltamethrin), from The Pesticide Manual, 11th Ed. (1997), The British Crop Protection Council, London, page 344;

(XVI) (4-chlorophenyl)-3-(2,6-difluorobenzoyl)urea (Diflubenzuron), from The Pesticide Manual, 11th Ed. (1997), The British Crop Protection Council, London, page 395;

(XVII) (1,4,5,6,7,7-Hexachloro-8,9,10-trinorbom-5-en-2,3-ylenebismethylene)-sulphite (Endosulfan), from The Pesticide Manual, 11th Ed. (1997), The British Crop Protection Council, London, page 459;

(XVIII) α-ethylthio-o-tolyl-methylcarbamate (Ethiofencarb), from The Pesticide Manual, 11th Ed. (1997), The British Crop Protection Council, London, page 479;

(XIX) O,O-dimethyl-O-4-nitro-m-tolyl-phosphorothioate (Fenitrothion), from The Pesticide Manual, 11th Ed. (1997), The British Crop Protection Council, London, page 514;

(XX) 2-secbutylphenyl-methylcarbamate (Fenobucarb), from The Pesticide Manual, 11th Ed. (1997), The British Crop Protection Council, London, page 516;

(XXI) (RS)-α-cyano-3-phenoxybenzyl-(RS)-2-(4-chlorophenyl)-3-methylbutyrate (Fenvalerate), from The Pesticide Manual, 11th Ed. (1997), The British Crop Protection Council, London, page 539;

(XXII) S[formyl(methyl)carbamoylmethyl]-O,O-dimethyl-phosphorodithioate (Formothion), from The Pesticide Manual, 11th Ed. (1997), The British Crop Protection Council, London, page 625;

(XXIII) 4-Methylthio-3,5-xylyl-methylcarbamate (Methlocarb), from The Pesticide Manual, 11th Ed. (1997), The British Crop Protection Council, London, page 813;

(XXIV) 7-Chlorobicyclo[3.2.0]hepta-2,6-dien-6-yl-dimethylphosphate (Heptenophos), from The Pesticide Manual, 11th Ed. (1997), The British Crop Protection Council, London, page 670;

(XXV) 1-(6-chloro-3-pyridylmethyl)-N-nitroimidazolidin-2-ylidenamine (Imidacloprid), from The Pesticide Manual, 11th Ed. (1997), The British Crop Protection Council, London, page 706;

(XXVI) 2-isopropylphenyl-methylcarbamate (Isoprocarb), from The Pesticide Manual, 11th Ed. (1997), The British Crop Protection Council, London, page 729;

(XXVII) O,S-dimethyl-phosphoramidothioate (Methamidophos), from The Pesticide Manual, 11th Ed. (1997), The British Crop Protection Council, London, page 808;

(XXVIII) S-Methyl-N(methylcarbamoyloxy)thioacetimidate (Methomyl), from The Pesticide Manual, 11th Ed. (1997), The British Crop Protection Council, London, page 815;

(XXIX) Methyl-3-(dimethoxyphosphinoyloxy)but-2-enoate (Mevinphos), from The Pesticide Manual, 11th Ed. (1997), The British Crop Protection Council, London, page 844;

(XXX) O,O-diethyl-O-4-nitrophenyl-phosphorothioate (Parathion), from The Pesticide Manual, 11th Ed. (1997), The British Crop Protection Council, London, page 926;

(XXXI) O,O-dimethyl-O-4-nitrophenyl-phosphorothioate (Parathion-methyl), from The Pesticide Manual, 11th Ed. (1997), The British Crop Protection Council, London, page 928;

(XXXII) S-6-chloro-2,3-dihydro-2-oxo-1,3-benzoxazol-3-ylmethyl-O,O-diethyl-phosphor-dithioate (Phosalone), from The PEsticide Manual, 11th Ed. (1997), The British Corp Protection Council, London, page 963;

(XXXIII) 2-Dimethylamino-5,6-dimethylpyrimidin-4-yl-dimethylcarbamate (Pirimicarb), from The Pesticide Manual, 11$^{th}$ Ed. (1997), The British Crop Protection Council, London, page 985;

(XXXIV) 2-isopropoxyphenyl-methylcarbamate (Propoxur), from The Pesticide Manual, 11$^{th}$ Ed. (1997), The British Crop Protection Council, London, page 1036;

(XXXV) 1-(3,5-dichloro-2,4-difluorophenyl)-3-(2,6-difluorobenzoyl)urea (Teflubenzuron), from The Pesticide Manual, 11$^{th}$ Ed. (1997), The British Crop Protection Council, London, page 1158;

(XXXVI) S-tert-butylthiomethyl-O,O-dimethyl-phosphorodithioate (Terbufos), from The Pesticide Manual, 11$^{th}$ Ed. (1997), The British Crop Protection Council, London, page 1165;

(XXXVII) ethyl-(3-tert.-butyl-1-dimethylcarbamoyl-1H-1,2,4-triazol-5-yl-thio)-acetate, (Triazamate), from The Pesticide Manual, 11$^{th}$ Ed. (1997), The British Crop Protection Council, London, page 1224;

(XXXVIII) Abamectin, from The Pesticide Manual, 11$^{th}$ Ed. (1997), The British Crop Protection Council, London, page 3;

(XXXIX) 2-sec-butylphenyl-methylcarbamate (Fenobucarb), from The Pesticide Manual, 11$^{th}$ Ed. (1997), The British Crop Protection Council, London, page 516;

(XL) N-tert.-butyl-N-(4-ethylbenzoyl)-3,5-dimethylbenzohydrazide (Tebufenozide), from The Pesticide Manual, 11$^{th}$ Ed. (1997), The British Crop Protection Council, London, page 1147;

(XLI) (±)-5-amino-1-(2,6-dichloro-α,α,α-trifluoro-p-tolyl)-4-trifluoromethyl-sulphinylpyrazol-3-carbonitrile (Fipronil), from The Pesticide Manual, 11$^{th}$ Ed. (1997), The British Crop Protection Council, London, page 545;

(XLII) (RS)-α-cyano-4-fluoro-3-phenoxybenzyl(1RS,3RS,1RS,3RS)3-(2,2-dichloro-vinyl)-2,2-dimethylcyclopropanecarboxylate (beta-Cyfluthrin), from The Pesticide Manual, 11$^{th}$ Ed. (1997), The British Crop Protection Council, London, page 295;

(XLIII) (4-ethoxyphenyl)-[3-(4-fluoro-3-phenoxyphenyl)propyl](dimethyl)silane (Silafluofen), from The Pesticide Manual, 11$^{th}$ Ed. (1997), The British Crop Protection Council, London, page 1105;

(XLIV) tert.-butyl (E)-α-(1,3-dimethyl-5-phenoxypyrazol-4-yl-methylenamino-oxy)-p-toluate (Fenpyroximate), from The Pesticide Manual, 11$^{th}$ Ed. (1997), The British Crop Protection Council, London, page 530;

(XLV) 2-tert.-butyl-5-(4-tert.-butylbenzylthio)-4-chloropyridazin-3(2H)-one (Pyridaben), from The Pesticide Manual, 11$^{th}$ Ed. (1997), The British Crop Protection Council, London, page 1161;

(XLVI) 4-[[4-(1,1-dimethylphenyl)phenyl]ethoxy]-quinazoline (Fenazaquin), from The Pesticide Manual, 11$^{th}$ Ed. (1997), The British Crop Protection Council, London, page 507;

(XLVII) 4-phenoxyphenyl-(RS)-2-(pyridyloxy)propyl-ether (Pyriproxyfen), from The Pesticide Manual, 11$^{th}$ Ed. (1997), The British Crop Protection Council, London, page 1073;

(XLVIII) 5-chloro-N-(2-[4-(2-ethoxyethyl)-2,3-dimethylphenoxy]ethyl)-6-ethylpyrimidine-4-amine (Pyrimidifen), from The Pesticide Manual, 11$^{th}$ Ed. (1997), The British Crop Protection Council, London, page 1070;

(XLIX) (E)-N-(6-chloro-3-pyridylmethyl)-(ethyl-N-methyl-2-nitrovinylidenediamine (Nitenpyram), from The Pesticide Manual, 11$^{th}$ ed. (1997), The British Crop Protection Council, London, page 880;

(L) (E)-N$^1$-[(6-chloro-3-pyridyl)methyl]-N$^2$-cyano-N$^1$-methylacetamidine (NI-25, Acetamiprid), from The Pesticide Manual, 11$^{th}$ Ed. (1997), The British Crop Protection Council, London, page 9;

(LI) Avermectin B$_1$, from The Pesticide Manual, 11$^{th}$ Ed. (1997), The British Crop Protection Council, London, page 3;

(LII) an insect-active extract from a plant, especially (2R, 6aS,12aS)-1,2,6,6a,12,12a-hexhydro-2-isopropenyl-8,9-dimethoxy-chromeno[3,4-b]furo[2,3-h]chromen-6-one (Rotenone), from The Pesticide Manual, 11$^{th}$ Ed. (1997), The British Crop Protection Council, London, page 1097; and an extract from *Azadirachta indica*, especially azadirachtin, from The Pesticide Manual, 11$^{th}$ Ed. (1997), The British Crop Protection Council, London, page 59; and (LIII) a preparation which contains insect-active nematodes, preferably *Heterorhabditis bacteriophora* and *Heterorhabditis megidis*, from The Pesticide Manual, 11$^{th}$ Ed. (1997), The British Crop Protection Council, London, page 671; *Steinemema feltiae*, from The Pesticide Manual, 11$^{th}$ Ed. (1997), The British Crop Protection Council, London, page 1115 and *Steinernema scapterisci*, from The Pesticide Manual, 11$^{th}$ Ed. (1997), The British Crop Protection Council, London, page 1116;

(LIV) a preparation obtainable from *Bacillus subtilis*, from The Pesticide Manual, 11$^{th}$ Ed. (1997), The British Crop Protection Council, London, page 72; or from a strain of *Bacillus thuringiensis* with the exception of compounds isolated from GC91 or from NCTC11821; The Pesticide Manual, 11$^{th}$ Ed. (1997), The British Crop Protection Council, London, page 73;

(LV) a preparation which contains insect-active fungi, preferably *Verticillium lecanii*, from The Pesticide Manual, 11$^{th}$ Ed. (1997), The British Crop Protection Council, London, page 1266; *Beauveria brogniarti*, from The Pesticide Manual, 11$^{th}$ Ed. (1997), The British Crop Protection Council, London, page 85 and *Beauveria bassiana*, from The Pesticide Manual, 11$^{th}$ Ed. (1997), The British Crop Protection Council, London, page 83;

(LVI) a preparation which contains insect-active viruses, preferably *Neodipridon Sertifer* NPV, from The Pesticide Manual, 11$^{th}$ Ed. (1997), The British Crop Protection Council, London, page 1342; *Mamestra brassicae* NPV, from The Pesticide Manual, 11$^{th}$ Ed. (1997), The British Crop Protection Council, London, page 759 and *Cydia pomonella granulosis* virus, from The Pesticide Manual, 11$^{th}$ Ed. (1997), The British Crop Protection Council, London, page 291;

(CLXXXI) 7-chloro-2,3,4a,5-tetrahydro-2-[methoxycarbonyl(4-trifluoromethoxyphenyl)-carbamoyl]indol[1,2e]oxazoline-4a-carboxylate (DPX-MP062, Indoxycarb), from The Pesticide Manual, 11$^{th}$ Ed. (1997), The British Crop Protection Council, London, page 453;

(CLXXXII) N-tert.-butyl-N'-(3,5-dimethylbenzoyl)-3-methoxy-2-methylbenzohydrazide (RH-2485, Methoxyfenozide), from The Pesticide Manual, 11$^{th}$ Ed. (1997), The British Crop Protection Council, London, page 1094; and (CLXXXIII) (N'-[4-methoxy-biphenyl-3-yl]-hydrazinecarboxylic acid isopropylester (D 2341), from Brighton Crop Protection Conference, 1996, 487-493;

(R2) Book of Abstracts, 212th ACS National Meeting Orlando, Fla., Aug. 25-29 (1996), AGRO-020. Publisher: American Chemical Society, Washington, D.C. CONEN: 63BFAF.

As a consequence of the above details, a further essential aspect of the present invention relates to combination preparations for the control of parasites on warm-blooded animals, characterized in that they contain, in addition to a compound of formula I, at least one further active ingredient having the same or different sphere of activity and at least one physiologically acceptable carrier. The present invention Is not restricted to two-fold combinations.

As a rule, the anthelminthic compositions according to the invention contain 0.1 to 99% by weight, especially 0.1 to 95% by weight of active ingredient of formula I, Ia or mixtures thereof, 99.9 to 1% by weight, especially 99.8 to 5% by weight of a solid or liquid admixture, including 0 to 25% by weight, especially 0.1 to 25% by weight of a surfactant.

Application of the compositions according to the invention to the animals to be treated may take place topically, perorally, parenterally or subcutaneously, the composition being present in the form of solutions, emulsions, suspensions, (drenches), powders, tablets, boli, capsules and pour-on formulations.

The pour-on or spot-on method consists in applying the compound of formula I to a specific location of the skin or coat, advantageously to the neck or backbone of the animal. This takes place e.g. by applying a swab or spray of the pour-on or spot-on formulation to a relatively small area of the coat, from where the active substance is dispersed almost automatically over wide areas of the fur owing to the spreading nature of the components in the formulation and assisted by the animal's movements.

Pour-on or spot-on formulations suitably contain carriers, which promote rapid dispersement over the skin surface or in the coat of the host animal, and are generally regarded as spreading oils. Suitable carriers are e.g. oily solutions; alcoholic and isopropanolic solutions such as solutions of 2-octyldodecanol or oleyl alcohol; solutions in esters of monocarboxylic acids, such as isopropyl myristate, isopropyl palmitate, lauric acid oxalate, oleic acid oleyl ester, oleic acid decyl ester, hexyl laurate, oleyl oleate, decyl oleate, capric acid esters of saturated fat alcohols of chain length $C_{12}$-$C_{18}$; solutions of esters of dicarboxylic acids, such as dibutyl phthalate, diisopropyl isophthalate, adipic acid diisopropyl ester, di-n-butyl adipate or also solutions of esters of aliphatic acids, e.g. glycols. It may be advantageous for a dispersing agent to be additionally present, such as one known from the pharmaceutical or cosmetic industry. Examples are 2-pyrrolidone, 2-(N-alkyl)pyrrolidone, acetone, polyethylene glycol and the ethers and esters thereof, propylene glycol or synthetic triglycerides.

The oily solutions include e.g. vegetable oils such as olive oil, groundnut oil, sesame oil, pine oil, linseed oil or castor oil. The vegetable oils may also be present in epoxidised form. Paraffins and silicone oils may also be used.

A pour-on or spot-on formulation generally contains 1 to 20% by weight of a compound of formula I, 0.1 to 50% by weight of dispersing agent and 45 to 98.9% by weight of solvent.

The pour-on or spot-on method is especially advantageous for use on herd animals such as cattle, horses, sheep or pigs, in which it is difficult or time-consuming to treat all the animals orally or by injection. Because of its simplicity, this method can of course also be used for all other animals, including individual domestic animals or pets, and is greatly favoured by the keepers of the animals, as it can often be carried out without the specialist presence of the veterinarian.

Whereas it is preferred to formulate commercial products as concentrates, the end user will normally use dilute formulations.

Such compositions may also contain further additives, such as stabilisers, anti-foaming agents, viscosity regulators, binding agents or tackifiers, as well as other active ingredients, in order to achieve special effects.

Anthelminthic compositions of this type, which are used by the end user, similarly form a constituent of the present invention.

In each of the processes according to the Invention for pest control or in each of the pest control compositions according to the invention, the active ingredients of formula I can be used in all of their steric configurations or in mixtures thereof.

The invention also includes a method of prophylactically protecting warm-blooded animals, especially productive livestock, domestic animals and pets, against parasitic helminths, which is characterized in that the active ingredients of the formula or the active ingredient formulations prepared therefrom are administered to the animals as an additive to the feed, or to the drinks or also in solid or liquid form, orally or by injection or parenterally. The invention also includes the compounds of formula I according to the invention for usage in one of the said processes.

The following examples serve merely to illustrate the invention without restricting it, the term active ingredient representing a substance listed in table 1.

In particular, preferred formulations are made up as follows:

(%=percent by weight)

Formulation Examples

1. Granulate

|  | a) | b) |
| --- | --- | --- |
| active ingredient | 5% | 10% |
| kaolin | 94% | — |
| highly dispersed silicic acid | 1% | — |
| attapulgite | — | 90% |

The active ingredient is dissolved in methylene chloride, sprayed onto the carrier and the solvent subsequently concentrated by evaporation under vacuum. Granulates of this kind can be mixed with the animal feed.

2. Granulate

| active ingredient | 3% |
| --- | --- |
| polyethylene glycol (mw 200) | 3% |
| kaolin | 94% |

(mw = molecular weight)

The finely ground active ingredient is evenly applied in a mixer to the kaolin which has been moistened with polyethylene glycol. In this way, dust-free coated granules are obtained.

3. Tablets or Boli

| I | active ingredient | 33.00% |
|---|---|---|
| | methylcellulose | 0.80% |
| | silicic acid, highly dispersed | 0.80% |
| | corn starch | 8.40% |
| II | lactose, cryst. | 22.50% |
| | corn starch | 17.00% |
| | microcryst. cellulose | 16.50% |
| | magnesium stearate | 1.00% |

I Methyl cellulose is stirred into water. After the material has swollen, silicic acid Is stirred in and the mixture homogeneously suspended. The active ingredient and the corn starch are mixed. The aqueous suspension Is worked into this mixture and kneaded to a dough. The resulting mass is granulated through a 12 M sieve and dried.

II All 4 excipients are mixed thoroughly.

III The preliminary mixes obtained according to I and II are mixed and pressed into tablets or boli.

4. Injectables

A. Oily Vehicle (Slow Release)

| 1. active ingredient | 0.1-1.0 g |
|---|---|
| groundnut oil | ad 100 ml |
| 2. active ingredient | 0.1-1.0 g |
| sesame oil | ad 100 ml |

Preparation: The active ingredient is dissolved in part of the oil whilst stirring and, if required, with gentle heating, then after cooling made up to the desired volume and sterile-filtered through a suitable membrane filter with a pore size of 0.22 μm.

B Water-Miscible Solvent (Average Rate of Release)

| active ingredient | 0.1-1.0 g |
|---|---|
| 4-hydroxymethyl-1,3-dioxolane (glycerol formal) | 40 g |
| 1,2-propanediol | ad 100 ml |
| active ingredient | 0.1-1.0 g |
| glycerol dimethyl ketal | 40 g |
| 1,2-propanediol | ad 100 ml |

Preparation: The active ingredient is dissolved in part of the solvent whilst stirring, made up to the desired volume and sterile-filtered through a suitable membrane filter with a pore size of 0.22 μm.

C. Aqueous Solubilisate (Rapid Release)

| 1. active ingredient | 0.1-1.0 g |
|---|---|
| polyethoxylated castor oil (40 ethylene oxide units) | 10 g |
| 1,2-propanediol | 20 g |
| benzyl alcohol | 1 g |
| aqua ad inject. | ad 100 ml |
| 2. active ingredient | 0.1-1.0 g |
| polyethoxylated sorbitan monooleate (20 ethylene oxide units) | 8 g |
| 4-hydroxymethyl-1,3-dioxolane (glycerol formal) | 20 g |
| benzyl alcohol | 1 g |
| aqua ad inject. | ad 100 ml |

Preparation: The active ingredient is dissolved in the solvents and the surfactant, and made up with water to the desired volume. Sterile filtration through an appropriate membrane filter of 0.22 μm pore size.

5. Pour On

A.

| active ingredient | 5 g |
|---|---|
| isopropyl myristate | 10 g |
| isopropanol | ad 100 ml |

B

| active ingredient | 2 g |
|---|---|
| hexyl laurate | 5 g |
| medium-chained triglyceride | 15 g |
| ethanol | ad 100 ml |

C.

| active ingredient | 2 g |
|---|---|
| oleyl oleate | 5 g |
| N-methyl-pyrrolidone | 40 g |
| isopropanol | ad 100 ml |

The aqueous systems may also preferably be used for oral and/or intraruminal application.

The compositions may also contain further additives, such as stabilisers, e.g. where appropriate epoxidised vegetable oils (epoxidised coconut oil, rapeseed oil, or soybean oil); antifoams, e.g. silicone oil, preservatives, viscosity regulators, binders, tackifiers, as well as fertilisers or other active ingredients to achieve special effects.

Further biologically active substances or additives, which are neutral towards the compounds of formula I and do not have a harmful effect on the host animal to be treated, as well as mineral salts or vitamins, may also be added to the described compositions.

The following examples serve to illustrate the invention. They do not limit the invention. The letter 'h' stands for hour.

Preparation Example

Example 1

N-[1-cyano-1-methyl-2-(5-chloro-2-(2,4-dichlorophenoxy)-Phenoxy)-ethyl]-4-trifluoromethoxyben

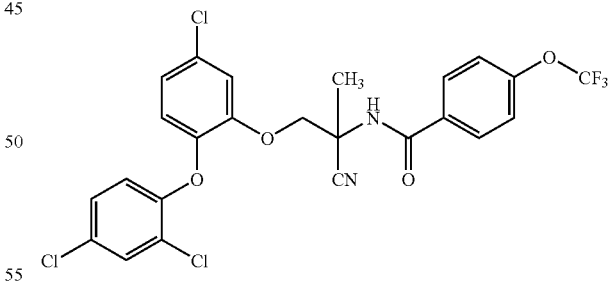

a) 5.79 g of 5-chloro-2-(2,4-dichlorophenoxy)-phenol, 2.31 g of chloroacetone, 3.04 g of potassium carbonate and 16 mg of potassium iodide are dissolved in 70 ml of acetone and boiled under reflux for 7 h. After cooling, the precipitate is filtered, concentrated by evaporation, the residue is stirred in hexane, filtered and concentrated by evaporation. In this way, 1-(5-chloro-2-(2,4-dichlorophenoxy)-phenoxy)-propan-2-one with a melting point of 64-65° is obtained.

b) 6.65 g of 1-(5-chloro-2-(2,4-dichlorophenoxy)-phenoxy)-propan-2-one and 0.98 g o sodium cyanide are suspended in a solution of 50 ml of aqueous 25% ammonia solution and 5 ml of ethanol, and stirred for 15 h at room temperture. The crude product is subsequently extracted from the reaction mixture with 100 ml of ethyl acetate, the organic phase is washed twice with saturated sodium chloride solution and water, dried with magnesium sulphate and concentrated by evaporation. 2-amino-3-(5-chloro-2-(2,4-dichlorophenoxy)-phenoxy)-2-methyl-pro is thus obtained.

c) A mixture of 193 mg of ethyl diisopropylamine, 12 mg of 4-dimethylaminopyridine and 323 mg of 4-(trifluoromethoxy)-benzoyl chloride is added dropwise at 0° C. to a solution of 445 mg of 2-amino-3-(5-chloro-2-(2,4-dichlorophenoxy)-phenoxy)-2-methyl-prop ionitrile in 25 ml of methylene chloride, and subsequently stirred for 24 h at room temperature.

Subsequently, the reaction mixture is diluted with 100 ml of ethyl acetate, then washed with a saturated sodium bicarbonate solution, water, aqueous 1N hydrochloric acid and finally with saturated sodium chloride solution. After drying the organic phase with magnesium sulphate and concentrating by evaporation, the residue is recrystallised in hexane. In this way, the title compound is obtained as white crystals with a melting point of 124-125° C.

The substances named In the following table may also be prepared analogously to the above-described method. The values of the melting points are given in ° C.

TABLE 1

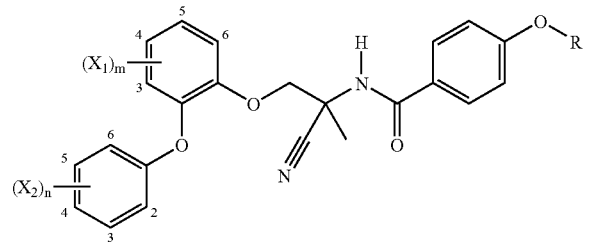

| No. | R | $(X_1)_m$ | $(X_2)_n$ | phys. data |
|---|---|---|---|---|
| 1.1 | $CF_3$ | 4-F | 2-F | |
| 1.2 | $CF_3$ | 4-F | 4-F | |
| 1.3 | $CF_3$ | 4-F | 2,4-$F_2$ | |
| 1.4 | $CF_3$ | 4-F | 2,5-$F_2$ | |
| 1.5 | $CF_3$ | 4-F | 3,4-$F_2$ | |
| 1.6 | $CF_3$ | 4-F | 3,5-$F_2$ | |
| 1.7 | $CF_3$ | 4-F | 2,3,5-$F_3$ | |
| 1.8 | $CF_3$ | 4-F | 2,4,6-$F_3$ | |
| 1.9 | $CF_3$ | 4-F | 2-Cl | |
| 1.10 | $CF_3$ | 4-F | 4-Cl | |
| 1.11 | $CF_3$ | 4-F | 2,4-$Cl_2$ | m.p: 52-3° |
| 1.12 | $CF_3$ | 4-F | 2,5-$Cl_2$ | |
| 1.13 | $CF_3$ | 4-F | 3,4-$Cl_2$ | |
| 1.14 | $CF_3$ | 4-F | 3,5-$Cl_2$ | |
| 1.15 | $CF_3$ | 4-F | 2,3,5-$Cl_3$ | |
| 1.16 | $CF_3$ | 4-F | 2,4,6-$Cl_3$ | |
| 1.17 | $CF_3$ | 4-F | 2,4-$F_2$, 5-Br | |
| 1.18 | $CF_3$ | 4-Cl | 2-F | |
| 1.19 | $CF_3$ | 4-Cl | 4-F | |
| 1.20 | $CF_3$ | 4-Cl | 2,4-$F_2$ | |
| 1.21 | $CF_3$ | 4-Cl | 2,5-$F_2$ | |
| 1.22 | $CF_3$ | 4-Cl | 3,4-$F_2$ | |
| 1.23 | $CF_3$ | 4-Cl | 3,5-$F_2$ | |
| 1.24 | $CF_3$ | 4-Cl | 2,3,5-$F_3$ | |
| 1.25 | $CF_3$ | 4-Cl | 2,4,6-$F_3$ | |
| 1.26 | $CF_3$ | 4-Cl | 2-Cl | |
| 1.27 | $CF_3$ | 4-Cl | 4-Cl | |
| 1.28 | $CF_3$ | 4-Cl | 2,4-$Cl_2$ | m.p: 136° |
| 1.29 | $CF_3$ | 4-Cl | 2,5-$Cl_2$ | |
| 1.30 | $CF_3$ | 4-Cl | 3,4-$Cl_2$ | |

TABLE 1-continued

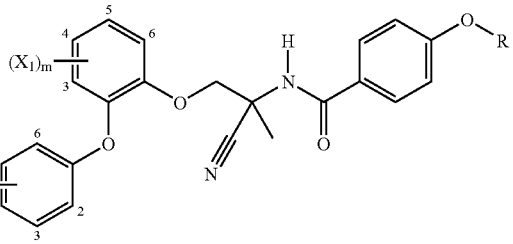

| No. | R | $(X_1)_m$ | $(X_2)_n$ | phys. data |
|---|---|---|---|---|
| 1.31 | $CF_3$ | 4-Cl | 3,5-$Cl_2$ | |
| 1.32 | $CF_3$ | 4-Cl | 2,3,5-$Cl_3$ | |
| 1.33 | $CF_3$ | 4-Cl | 2,4,6-$Cl_3$ | |
| 1.34 | $CF_3$ | 4-Cl | 2,4-$F_2$, 5-Br | |
| 1.35 | $CF_3$ | 5-F | 2-F | |
| 1.36 | $CF_3$ | 5-F | 4-F | |
| 1.37 | $CF_3$ | 5-F | 2,4-$F_2$ | |
| 1.38 | $CF_3$ | 5-F | 2,5-$F_2$ | |
| 1.39 | $CF_3$ | 5-F | 3,4-$F_2$ | |
| 1.40 | $CF_3$ | 5-F | 3,5-$F_2$ | |
| 1.41 | $CF_3$ | 5-F | 2,3,5-$F_3$ | |
| 1.42 | $CF_3$ | 5-F | 2,4,6-$F_3$ | |
| 1.43 | $CF_3$ | 5-F | 2-Cl | |
| 1.44 | $CF_3$ | 5-F | 4-Cl | |
| 1.45 | $CF_3$ | 5-F | 2,4-$Cl_2$ | m.p: 106-8° |
| 1.46 | $CF_3$ | 5-F | 2,5-$Cl_2$ | |
| 1.47 | $CF_3$ | 5-F | 3,4-$Cl_2$ | |
| 1.48 | $CF_3$ | 5-F | 3,5-$Cl_2$ | |
| 1.49 | $CF_3$ | 5-F | 2,3,5-$Cl_3$ | |
| 1.50 | $CF_3$ | 5-F | 2,4,6-$Cl_3$ | |
| 1.51 | $CF_3$ | 5-F | 2,4-$F_2$, 5-Br | |
| 1.52 | $CF_3$ | 5-Cl | 2-F | |
| 1.53 | $CF_3$ | 5-Cl | 4-F | |
| 1.54 | $CF_3$ | 5-Cl | 2,4-$F_2$ | |
| 1.55 | $CF_3$ | 5-Cl | 2,5-$F_2$ | |
| 1.56 | $CF_3$ | 5-Cl | 3,4-$F_2$ | |
| 1.57 | $CF_3$ | 5-Cl | 3,5-$F_2$ | white cryst. |
| 1.58 | $CF_3$ | 5-Cl | 2,3,5-$F_3$ | |
| 1.59 | $CF_3$ | 5-Cl | 2,4,6-$F_3$ | m.p: 131-2° |
| 1.60 | $CF_3$ | 5-Cl | 2-Cl | |
| 1.61 | $CF_3$ | 5-Cl | 4-Cl | white cryst. |
| 1.62 | $CF_3$ | 5-Cl | 2,4-$Cl_2$ | m.p: 124-5° |
| 1.63 | $CF_3$ | 5-Cl | 2,5-$Cl_2$ | vitreous |
| 1.64 | $CF_3$ | 5-Cl | 3,4-$Cl_2$ | m.p: 104-5° |
| 1.65 | $CF_3$ | 5-Cl | 3,5-$Cl_2$ | m.p: 112-3° |
| 1.66 | $CF_3$ | 5-Cl | 2,3,5-$Cl_3$ | |
| 1.67 | $CF_3$ | 5-Cl | 2,4,6-$Cl_3$ | |
| 1.68 | $CF_3$ | 5-Cl | 2,4-$F_2$, 5-Br | m.p: 82-4° |
| 1.69 | $CF_3$ | 4,5-$F_2$ | 2-F | |
| 1.70 | $CF_3$ | 4,5-$F_2$ | 4-F | |
| 1.71 | $CF_3$ | 4,5-$F_2$ | 2,4-$F_2$ | |
| 1.72 | $CF_3$ | 4,5-$F_2$ | 2,5-$F_2$ | |
| 1.73 | $CF_3$ | 4,5-$F_2$ | 3,4-$F_2$ | |
| 1.74 | $CF_3$ | 4,5-$F_2$ | 3,5-$F_2$ | |
| 1.75 | $CF_3$ | 4,5-$F_2$ | 2,3,5-$F_3$ | m.p: 78-80° |
| 1.76 | $CF_3$ | 4,5-$F_2$ | 2,4,6-$F_3$ | |
| 1.77 | $CF_3$ | 4,5-$F_2$ | 2-Cl | vitreous |
| 1.78 | $CF_3$ | 4,5-$F_2$ | 4-Cl | |
| 1.79 | $CF_3$ | 4,5-$F_2$ | 2,4-$Cl_2$ | m.p: 80-3° |
| 1.80 | $CF_3$ | 4,5-$F_2$ | 2,5-$Cl_2$ | |
| 1.81 | $CF_3$ | 4,5-$F_2$ | 3,4-$Cl_2$ | white cryst. |
| 1.82 | $CF_3$ | 4,5-$F_2$ | 3,5-$Cl_2$ | m.p: 126-7° |
| 1.83 | $CF_3$ | 4,5-$F_2$ | 2,3,5-$Cl_3$ | |
| 1.84 | $CF_3$ | 4,5-$F_2$ | 2,4,6-$Cl_3$ | |
| 1.85 | $CF_3$ | 4,5-$F_2$ | 2,4-$F_2$, 5-Br | |
| 1.86 | $CF_3$ | 4,5-$Cl_2$ | 2-F | |
| 1.87 | $CF_3$ | 4,5-$Cl_2$ | 4-F | |
| 1.88 | $CF_3$ | 4,5-$Cl_2$ | 2,4-$F_2$ | |
| 1.89 | $CF_3$ | 4,5-$Cl_2$ | 2,5-$F_2$ | |
| 1.90 | $CF_3$ | 4,5-$Cl_2$ | 3,4-$F_2$ | |
| 1.91 | $CF_3$ | 4,5-$Cl_2$ | 3,5-$F_2$ | |
| 1.92 | $CF_3$ | 4,5-$Cl_2$ | 2,3,5-$F_3$ | |
| 1.93 | $CF_3$ | 4,5-$Cl_2$ | 2,4,6-$F_3$ | |
| 1.94 | $CF_3$ | 4,5-$Cl_2$ | 2-Cl | |

TABLE 1-continued

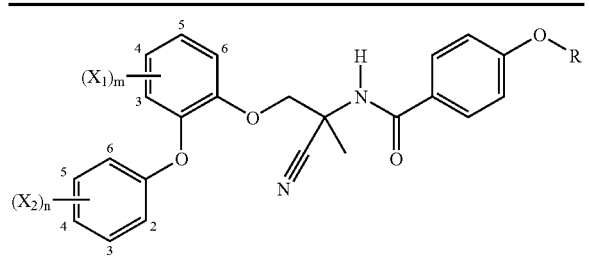

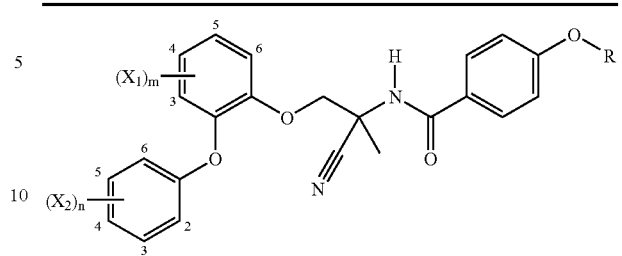

| No. | R | (X₁)ₘ | (X₂)ₙ | phys. data |
|---|---|---|---|---|
| 1.95 | CF₃ | 4,5-Cl₂ | 4-Cl | |
| 1.96 | CF₃ | 4,5-Cl₂ | 2,4-Cl₂ | m.p: 118° |
| 1.97 | CF₃ | 4,5-Cl₂ | 2,5-Cl₂ | |
| 1.98 | CF₃ | 4,5-Cl₂ | 3,4-Cl₂ | |
| 1.99 | CF₃ | 4,5-Cl₂ | 3,5-Cl₂ | |
| 1.100 | CF₃ | 4,5-Cl₂ | 2,3,5-Cl₃ | |
| 1.101 | CF₃ | 4,5-Cl₂ | 2,4,6-Cl₃ | |
| 1.102 | CF₃ | 4,5-Cl₂ | 2,4-F₂, 5-Br | |
| 1.103 | CF₃ | 4-Cl, 5-F | 2-F | |
| 1.104 | CF₃ | 4-Cl, 5-F | 4-F | |
| 1.105 | CF₃ | 4-Cl, 5-F | 2,4-F₂ | |
| 1.106 | CF₃ | 4-Cl, 5-F | 2,5-F₂ | |
| 1.107 | CF₃ | 4-Cl, 5-F | 3,4-F₂ | |
| 1.108 | CF₃ | 4-Cl, 5-F | 3,5-F₂ | |
| 1.109 | CF₃ | 4-Cl, 5-F | 2,3,5-F₃ | |
| 1.110 | CF₃ | 4-Cl, 5-F | 2,4,6-F₃ | |
| 1.111 | CF₃ | 4-Cl, 5-F | 2-Cl | |
| 1.112 | CF₃ | 4-Cl, 5-F | 4-Cl | |
| 1.113 | CF₃ | 4-Cl, 5-F | 2,4-Cl₂ | amorph |
| 1.114 | CF₃ | 4-Cl, 5-F | 2,5-Cl₂ | |
| 1.115 | CF₃ | 4-Cl, 5-F | 3,4-Cl₂ | |
| 1.116 | CF₃ | 4-Cl, 5-F | 3,5-Cl₂ | |
| 1.117 | CF₃ | 4-Cl, 5-F | 2,3,5-Cl₃ | |
| 1.118 | CF₃ | 4-Cl, 5-F | 2,4,6-Cl₃ | |
| 1.119 | CF₃ | 4-Cl, 5-F | 2,4-F₂, 5-Br | |
| 1.120 | C₂F₅ | 5-F | 2-F | |
| 1.121 | C₂F₅ | 5-F | 4-F | |
| 1.122 | C₂F₅ | 5-F | 2,4-F₂ | |
| 1.123 | C₂F₅ | 5-F | 2,5-F₂ | |
| 1.124 | C₂F₅ | 5-F | 3,4-F₂ | |
| 1.125 | C₂F₅ | 5-F | 3,5-F₂ | |
| 1.126 | C₂F₅ | 5-F | 2,3,5-F₃ | |
| 1.127 | C₂F₅ | 5-F | 2,4,6-F₃ | |
| 1.128 | C₂F₅ | 5-F | 2-Cl | |
| 1.129 | C₂F₅ | 5-F | 4-Cl | |
| 1.130 | C₂F₅ | 5-F | 2,4-Cl₂ | |
| 1.131 | C₂F₅ | 5-F | 2,5-Cl₂ | |
| 1.132 | C₂F₅ | 5-F | 3,4-Cl₂ | |
| 1.133 | C₂F₅ | 5-F | 3,5-Cl₂ | |
| 1.134 | C₂F₅ | 5-F | 2,3,5-Cl₃ | |
| 1.135 | C₂F₅ | 5-F | 2,4,6-Cl₃ | |
| 1.136 | C₂F₅ | 5-F | 2,4-F₂, 5-Br | |
| 1.137 | C₂F₅ | 5-Cl | 2-F | |
| 1.138 | C₂F₅ | 5-Cl | 4-F | |
| 1.139 | C₂F₅ | 5-Cl | 2,4-F₂ | |
| 1.140 | C₂F₅ | 5-Cl | 2,5-F₂ | |
| 1.141 | C₂F₅ | 5-Cl | 3,4-F₂ | |
| 1.142 | C₂F₅ | 5-Cl | 3,5-F₂ | |
| 1.143 | C₂F₅ | 5-Cl | 2,3,5-F₃ | |
| 1.144 | C₂F₅ | 5-Cl | 2,4,6-F₃ | |
| 1.145 | C₂F₅ | 5-Cl | 2-Cl | |
| 1.146 | C₂F₅ | 5-Cl | 4-Cl | |
| 1.147 | C₂F₅ | 5-Cl | 2,4-Cl₂ | |
| 1.148 | C₂F₅ | 5-Cl | 2,5-Cl₂ | |
| 1.149 | C₂F₅ | 5-Cl | 3,4-Cl₂ | |
| 1.150 | C₂F₅ | 5-Cl | 3,5-Cl₂ | |
| 1.151 | C₂F₅ | 5-Cl | 2,3,5-Cl₃ | |
| 1.152 | C₂F₅ | 5-Cl | 2,4,6-Cl₃ | |
| 1.153 | C₂F₅ | 5-Cl | 2,4-F₂, 5-Br | |
| 1.154 | C₂F₅ | 4,5-F₂ | 2-F | |
| 1.155 | C₂F₅ | 4,5-F₂ | 4-F | |
| 1.156 | C₂F₅ | 4,5-F₂ | 2,4-F₂ | |
| 1.157 | C₂F₅ | 4,5-F₂ | 2,5-F₂ | |
| 1.158 | C₂F₅ | 4,5-F₂ | 3,4-F₂ | |
| 1.159 | C₂F₅ | 4,5-F₂ | 3,5-F₂ | |
| 1.160 | C₂F₅ | 4,5-F₂ | 2,3,5-F₃ | |
| 1.161 | C₂F₅ | 4,5-F₂ | 2,4,6-F₃ | |
| 1.162 | C₂F₅ | 4,5-F₂ | 2-Cl | |
| 1.163 | C₂F₅ | 4,5-F₂ | 4-Cl | |
| 1.164 | C₂F₅ | 4,5-F₂ | 2,4-Cl₂ | |
| 1.165 | C₂F₅ | 4,5-F₂ | 2,5-Cl₂ | |
| 1.166 | C₂F₅ | 4,5-F₂ | 3,4-Cl₂ | |
| 1.167 | C₂F₅ | 4,5-F₂ | 3,5-Cl₂ | |
| 1.168 | C₂F₅ | 4,5-F₂ | 2,3,5-Cl₃ | |
| 1.169 | C₂F₅ | 4,5-F₂ | 2,4,6-Cl₃ | |
| 1.170 | C₂F₅ | 4,5-F₂ | 2,4-F₂, 5-Br | |
| 1.171 | C₂F₅ | 4,5-Cl₂ | 2-F | |
| 1.172 | C₂F₅ | 4,5-Cl₂ | 4-F | |
| 1.173 | C₂F₅ | 4,5-Cl₂ | 2,4-F₂ | |
| 1.174 | C₂F₅ | 4,5-Cl₂ | 2,5-F₂ | |
| 1.175 | C₂F₅ | 4,5-Cl₂ | 3,4-F₂ | |
| 1.176 | C₂F₅ | 4,5-Cl₂ | 3,5-F₂ | |
| 1.177 | C₂F₅ | 4,5-Cl₂ | 2,3,5-F₃ | |
| 1.178 | C₂F₅ | 4,5-Cl₂ | 2,4,6-F₃ | |
| 1.179 | C₂F₅ | 4,5-Cl₂ | 2-Cl | |
| 1.180 | C₂F₅ | 4,5-Cl₂ | 4-Cl | |
| 1.181 | C₂F₅ | 4,5-Cl₂ | 2,4-Cl₂ | |
| 1.182 | C₂F₅ | 4,5-Cl₂ | 2,5-Cl₂ | |
| 1.183 | C₂F₅ | 4,5-Cl₂ | 3,4-Cl₂ | |
| 1.184 | C₂F₅ | 4,5-Cl₂ | 3,5-Cl₂ | |
| 1.185 | C₂F₅ | 4,5-Cl₂ | 2,3,5-Cl₃ | |
| 1.186 | C₂F₅ | 4,5-Cl₂ | 2,4,6-Cl₃ | |
| 1.187 | C₂F₅ | 4,5-Cl₂ | 2,4-F₂, 5-Br | |
| 1.188 | C₂F₅ | 4-Cl, 5-F | 2-F | |
| 1.189 | C₂F₅ | 4-Cl, 5-F | 4-F | |
| 1.190 | C₂F₅ | 4-Cl, 5-F | 2,4-F₂ | |
| 1.191 | C₂F₅ | 4-Cl, 5-F | 2,5-F₂ | |
| 1.192 | C₂F₅ | 4-Cl, 5-F | 3,4-F₂ | |
| 1.193 | C₂F₅ | 4-Cl, 5-F | 3,5-F₂ | |
| 1.194 | C₂F₅ | 4-Cl, 5-F | 2,3,5-F₃ | |
| 1.195 | C₂F₅ | 4-Cl, 5-F | 2,4,6-F₃ | |
| 1.196 | C₂F₅ | 4-Cl, 5-F | 2-Cl | |
| 1.197 | C₂F₅ | 4-Cl, 5-F | 4-Cl | |
| 1.198 | C₂F₅ | 4-Cl, 5-F | 2,4-Cl₂ | |
| 1.199 | C₂F₅ | 4-Cl, 5-F | 2,5-Cl₂ | |
| 1.200 | C₂F₅ | 4-Cl, 5-F | 3,4-Cl₂ | |
| 1.201 | C₂F₅ | 4-Cl, 5-F | 3,5-Cl₂ | |
| 1.202 | C₂F₅ | 4-Cl, 5-F | 2,3,5-Cl₃ | |
| 1.203 | C₂F₅ | 4-Cl, 5-F | 2,4,6-Cl₃ | |
| 1.204 | C₂F₅ | 4-Cl, 5-F | 2,4-F₂, 5-Br | |

BIOLOGICAL EXAMPLES

1. In-Vivo Test on *Trichostronqylus colubriformis* and *Haemonchus contortus* on Mongolian Gerbils (*Meriones unauiculatus*) using Peroral Application Six to eight week old Mongolian gerbils are infected through a stomach tube with ca. 2000 third instar larvae each of *T. colubriformis* and *H. contortus*. 6 days after infection, the gerbils are treated by peroral application with the test compounds, dissolved in a mixture of 2 parts DMSO and 1 part polyethylene glycol (PEG 400), in quantities of 100, 32 and 10-0.1 mg/kg. On day 9 (3 days after treatment), when most of the *H. contortus* that are still present are late 4th instar larvae and most of the *T. colubriformis* are immature adults, the gerbils are killed in order to count the worms. The efficacy is calculated as the % reduction of the number of worms in each gerbil, compared with the geometric average of number of worms from 6 infected and untreated gerbils.

In this test, a vast reduction In nematode infestation is achieved with compounds of formula I. In particular, compound 1.18 from Table 1 effects complete elimination of the nematode infestation at a dose of 16 mg/kg.

To examine the insecticidal and/or acaricidal activity of the compounds of formula I on animals and plants, the following test methods may be used.

2. Activity on $L_1$ larvae of *Lucilia sericata*

1 ml of an aqueous suspension of the active substance to be tested is admixed with 3 ml of a special larvae growth medium at ca. 50° C., so that a homogenate of either 250 or 125 ppm of active ingredient content is obtained. Ca. 30 *Lucilia larvae* ($L_1$) are used in each test tube sample. After 4 days, the mortality rate is determined.

3. Acaricidal Activity on *Boophilus microplus* (Biarra strain)

A piece of sticky tape is attached horizontally to a PVC sheet, so that 10 fully engorged female ticks of *Boophilus microplus* (Biarra strain) can be adhered thereto by their backs, side by side, in a row. Using an injection needle, 1 µl of a liquid is injected into each tick. The liquid is a 1:1 mixture of polyethylene glycol and acetone and it contains, dissolved therein, a certain amount of active ingredient chosen from 1, 0.1 or 0.01 µg per tick. Control animals are given an injection without active ingredient. After treatment, the animals are kept under normal conditions in an insectarium at ca. 28° C. and at 80% relative humidity until oviposition takes place and the larvae have hatched from the eggs of the control animals. The activity of a tested substance is determined by $IR_{90}$, i.e. an evaluation is made of the dosage of active ingredient at which 9 out of 10 female ticks (=90%) lay eggs that are infertile even after 30 days.

4. In Vitro Efficacy on Engorged Female *Boophilus microplus* (BIARRA):

4×10 engorged female ticks of the OP-resistant BIARRA strain are adhered to a sticky strip and covered for 1 hour with a cotton-wool ball soaked in an emulsion or suspension of the test compound in concentrations of 500, 125, 31 and 8 ppm respectively. Evaluation takes place 28 days later based on mortality, oviposition and hatched larvae. An indication of the activity of the test compounds is shown by the number of females that die quickly before laying eggs,
  survive for some time without laying eggs,
  lay eggs in which no embryos are formed,
  lay eggs in which embryos form, from which no larvae hatch, and
  lay eggs In which embryos form, from which larvae normally hatch within 26 to 27 days.

5. In Vitro Efficacy on Nymphs of *Amblyomma hebraeum*

About 5 fasting nymphs are placed In a polystyrene test tube containing 2 ml of the test compound in solution, suspension or emulsion.

After immersion for 10 minutes, and shaking for 2×10 seconds on a vortex mixer, the test tubes are blocked up with a tight wad of cotton wool and rotated. As soon as all the liquid has been soaked up by the cotton wool ball, it is pushed half-way into the test tube which is still being rotated, so that most of the liquid is squeezed out of the cotton-wool ball and flows into a Petri dish below.

The test tubes are then kept at room temperature in a room with daylight until evaluated. After 14 days, the test tubes are immersed in a beaker of boiling water. If the ticks begin to move in reaction to the heat, the test substance is inactive at the tested concentration, otherwise the ticks are regarded as dead and the test substances regarded as active at the tested concentration. All substances are tested in a concentration range of 0.1 to 100 ppm.

6. Activity against *Dermanyssus gallinae*

2 to 3 ml of a solution containing 10 ppm active ingredient, and ca. 200 mites (*Dermanyssus gallinae*) at different stages of development are added to a glass container which is open at the top. Then the container is closed with a wad of cotton wool, shaken for 10 minutes until the mites are completely wet, and then inverted briefly so that the remaining test solution can be absorbed by the cotton wool. After 3 days, the mortality of the mites is determined by counting the dead individuals and indicated as a percentage.

7. Activity against *Musca domestica*

A sugar cube is treated with a solution of the test substance in such a way that the concentration of test substance in the sugar, after drying over night, is 250 ppm. The cube treated in this way is placed on an aluminium dish with wet cotton wool and 10 adult *Musca domestica* of an OP-resistant strain, covered with a beaker and incubated at 25° C. The mortality rate is determined after 24 hours.

We claim:

1. A compound of formula I

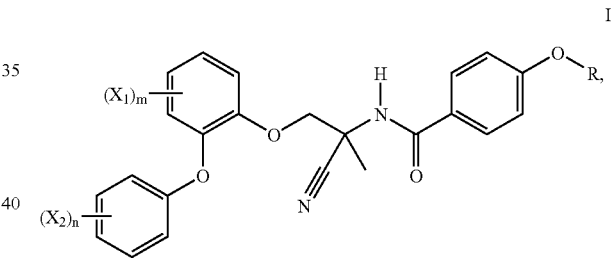

wherein

R signifies $C_1$-$C_6$-alkyl, halo-$C_1$-$C_6$-alkyl, $C_1$-$C_6$-alkoxy-$C_2$-$C_6$-alkyl or halo-$C_1$-$C_6$-alkoxy-halo-$C_2$-$C_6$-alkyl;

$X_1$ signifies halogen, whereby if m is greater than 1, $X_1$ may be variable halogen;

$X_2$ signifies halogen, whereby if n is greater than 1, $X_2$ may be variable halogen;

m signifies 1, 2, 3 or 4; and n is 1, 2, 3, 4 or 5.

2. A compound of formula I, according to claim 1, wherein R is $C_1$-$C_6$-alkyl or halo-$C_1$-$C_6$-alkyl.

3. A compound of formula I, according to claim 1, wherein R is halo-$C_1$-$C_4$-alkyl.

4. A compound of formula I, according to claim 1, wherein R is halo-$C_1$-$C_2$-alkyl.

5. A compound of formula I according to claim 1, wherein $X_1$ is chlorine or fluorine.

6. A compound of formula I according to claim 1, wherein $X_1$ is chlorine.

7. A compound of formula I according to claim 1, wherein $X_2$ is chlorine or fluorine.

8. A compound of formula I according to claim 1, wherein $X_2$ is chlorine.

9. A compound of formula I according to claim 1, wherein m is 1, 2 or 3.

10. A compound of formula I according to claim 1, wherein m is 1 or 2.

11. A compound of formula I according to claim 1, wherein m is 1.

12. A compound of formula I according to claim 1, wherein n is 1, 2 or 3.

13. A compound of formula I according to claim 1, wherein n is 1 or 2.

14. A compound of formula I according to claim 1, wherein n is 2.

15. A compound of formula I, according to claim 1, wherein R is $C_1$-$C_6$-alkyl or halo-$C_1$-$C_6$-alkyl;
$X_1$ signifies chlorine or fluorine;
$X_2$ signifies chlorine or fluorine;
m is 1, 2 or 3 and
n is 1, 2 or 3.

16. A compound of formula I, according to claim 1, wherein R is halo-$C_1$-$C_4$-alkyl;
$X_1$ and $X_2$ are chlorine;
m is 1 or 2, and
n is 1 or 2.

17. A compound of formula I, according to claim 1, wherein R is halo-$C_1$-$C_2$-alkyl;
$X_1$ and $X_2$ are chlorine;
m is 1, and
n is 2.

18. A compound of formula I according to claim 1 having the name N-[1-cyano-1-methyl-2-(5-chloro-2-{2,4-dichlorophenoxy-phenoxy}-ethyl]-4-trifluoromethoxybe.

19. Process for the preparation of compounds of formula I, respectively in free form or in salt form, according to claim 1, whereby a compound of formula II

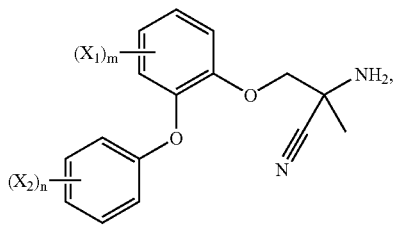

which is known or may be produced analogously to corresponding known compounds, and wherein $X_1$, $X_2$, m and n are defined as given for formula I, is reacted with a compound of formula III

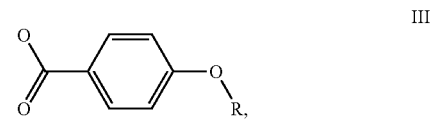

which is known or may be prepared analogously to corresponding known compounds, and wherein R is defined as given for formula I and Q is a leaving group, optionally in the presence of a basic catalyst, and if desired, a compound of formula I obtainable according to the method or in another way, respectively in free form or in salt form, is converted into another compound of formula I, a mixture of isomers obtainable according to the method is separated and the desired isomer isolated and/or a free compound of formula I obtainable according to the method is converted into a salt or a salt of a compound of formula I obtainable according to the method is converted into the free compound of formula I or into another salt.

20. Composition for the control of parasites, which contains as active ingredient at least one compound of formula I according to claim 1, in addition to carriers and/or dispersants.

21. A method of treating an animal for parasites comprising administering to said animal in need of treatment thereof a parasiticidal effective amount of the composition of claim 20.

22. The method of claim 21 wherein said administration to said animal is topically, perorally, parenterally, or subcutaneously.

23. A method of claim 21 wherein said composition of claim 21 is in a formulation consisting of the group of pour-on, spot-on, tablet, chewie, powder, boli, capsules, suspension, emulsion, solution, injectable, water-additive, and food-additive.

24. The method of claim 21 wherein said parasites are endo-parasites.

25. The method of claim 24 wherein said endo-parasites are helminthes.

* * * * *